US010233504B2

(12) United States Patent
Winchell et al.

(10) Patent No.: US 10,233,504 B2
(45) Date of Patent: Mar. 19, 2019

(54) METHODS AND COMPOSITIONS FOR ISOTHERMAL AMPLIFICATION AND DETECTION OF MYCOPLASMA PNEUMONIAE (71) Applicants: The United States of America, as represented by the Secretary, Dept. of Health and Human Services, Washington, DC (US); P3S Corporation, San Antonio, TX (US)

(72) Inventors: Jonas M. Winchell, Lilburn, GA (US); Brianna Petrone, Durham, NC (US); Maureen H. Diaz, Atlanta, GA (US); Bernard J. Wolff, Roswell, GA (US)

(73) Assignees: The United States of America, as represented by the Secretary, Department of Health and Human Services, Washington, DC (US); P3S Corporation, San Antonio, TX (US)

( * ) Notice: Subject to any disclaimer, the term of this patent is extended or adjusted under 35 U.S.C. 154(b) by 238 days.

(21) Appl. No.: 15/043,194

(22) Filed: Feb. 12, 2016

(65) Prior Publication Data
US 2016/0237479 A1 Aug. 18, 2016

Related U.S. Application Data
(60) Provisional application No. 62/116,166, filed on Feb. 13, 2015.

(51) Int. Cl.
 C12P 19/34 (2006.01)
 C12Q 1/689 (2018.01)
 C12Q 1/6844 (2018.01)
(52) U.S. Cl.
 CPC ........... *C12Q 1/689* (2013.01); *C12Q 1/6844* (2013.01)
(58) Field of Classification Search
 CPC ............ C12Q 1/6844; C12Q 2525/301; C12Q 2531/119; C12Q 1/689
 USPC ....................................................... 435/91.2
 See application file for complete search history.

(56) References Cited

U.S. PATENT DOCUMENTS 7,622,571 B2 11/2009 Baseman et al.

FOREIGN PATENT DOCUMENTS

| CN | 101665826 | 3/2010 |
| CN | 101665827 | 3/2010 |
| CN | 102618655 | 8/2012 |
| CN | 103276083 | 9/2013 |
| JP | 2006158220 | 6/2006 |
| JP | 5204466 | 6/2009 |
| WO | WO 2005032491 | * 4/2005 |
| WO | WO 2011/133433 | 10/2011 |

OTHER PUBLICATIONS

Saito et al., Journal of Meidcal Microbiology, 54, 1037-1041, (Year: 2005).*
Torres et al., BMC Bioinformatics, 12: 240, pp. 1-7 (Year: 2011).*
Notomi et al., Nucleic acid Research ., 28 (12), e63, i-vii, (Year: 2000).*
Kannan et al., PNAS, 103(17), pp. 6724-6729 (Year: 2006).*
Himmelreich et al., NAR, 24 (13, pp. 4420-4449 (Year: 1996).*
Aizawa et al., "Clinical utility of loop-mediated isothermal amplification for rapid diagnosis of Mycoplasma pneumoniae in children," *Journal of Medical Microbiology*, vol. 63, pp. 248-251, 2014.
Genbank, "Mycoplasma pneumoniae strain M129 CARDS toxin gene, complete cds," Accession No. DQ447750.1, Apr. 28, 2006 (2 pages).
Gotoh et al., Detection of *Mycoplasma pneumoniae* by loop-mediated isothermal amplification (LAMP) assay and serology in pediatric community-acquired pneumonia, *J. Infect. Chemother.*, vol. 18, pp. 662-667, 2012.
Illumingene, "Mycoplasma DNA Amplification Assay," 2013 (21 pages).
Kakuya et al., "Genetic point-of-care diagnosis of *Mycoplasma pneumoniae* infection using LAMP assay," *Pediatrics International*, vol. 56, pp. 547-552, 2014.
Mori et al., "Loop-mediated isothermal amplification (LAMP): a rapid, accurate, and cost-effective diagnostic method for infectious diseases," *J. Infect. Chemother.*, vol. 15, pp. 62-69, 2009.
Mori et al., "Loop-mediated isothermal amplification (LAMP): recent progress in research and development," *J. Infect. Chemother.*, vol. 19, No. 3, pp. 404-411, 2013.
Petrone et al., "Detection of *Mycoplasma pneumoniae* directly from clinical specimens using a colorimetric loop-mediated isothermal amplification assay," Poster, *114th General Meeting of the American Society for Microbiology*, May 17-20, 2014 (1 page).
Petrone et al., "Detection of *Mycoplasma pneumoniae* directly from clinical specimens using a colorimetric loop-mediated isothermal amplification assay," Abstract G-1678, *114th General Meeting of the American Society for Microbiology*, May 17-20, 2014 (Abstract, 1 page).
Petrone et al., "Isothermal Detection of *Mycoplasma pneumoniae* Directly from Respiratory Clinical Specimens," *J. Clin. Microbiol.* vol. 53, No. 9, pp. 2970-2976, 2015.
Ratliff et al., "Comparison of the illumigene Mycoplasma DNA Amplification Assay and Culture for Detection of *Mycoplasma pneumoniae*," *Journal of Clinical Microbiology*, vol. 52, No. 4, pp. 1060-1063, 2014.

(Continued)

*Primary Examiner* — Cynthia B Wilder
(74) *Attorney, Agent, or Firm* — Klarquist Sparkman, LLP (57) ABSTRACT

Disclosed herein are methods and compositions (e.g., oligonucleotide primers) for isothermal amplification and detection of *M. pneumoniae* nucleic acids in a sample. In some embodiments, the methods include contacting a sample with a set of LAMP primers specific for a *M. pneumoniae* CARDS toxin-encoding nucleic acid under conditions sufficient to produce an *M. pneumoniae* nucleic acid amplification product and detecting the resulting *M. pneumoniae* amplification product. Kits including sets of LAMP primers for detection of *M. pneumoniae* CARDS toxin nucleic acids are also provided herein.

12 Claims, 5 Drawing Sheets

Specification includes a Sequence Listing.

(56) References Cited

OTHER PUBLICATIONS

Saito et al., "Development and evaluation of a loop-mediated isothermal amplification assay for rapid detection of *Mycoplasma pneumoniae*," *Journal of Medical Microbiology*, vol. 54, pp. 1037-1041, 2005.

Tomita et al., "Loop-mediated isothermal amplification (LAMP) of gene sequences and simple visual detection of products," *Nature Protocols*, vol. 3, No. 5, pp. 877-882, 2008.

Winchell et al., "Detection of *Mycoplasma pneumoniae* using isothermal amplification: towards a point-of-care device for clinicians," Abstract, *20th Congress of the International Organization for Mycoplasmology*, Jun. 1-6, 2014 (4 pages).

Winchell et al., "Detection of *Mycoplasma pneumoniae* using isothermal amplification: towards a point-of-care device for clinicians," Presentation, *20th Congress of the International Organization for Mycoplasmology*, Jun. 1-6, 2014 (32 pages).

Yoshino et al., Sensitive and rapid detection of Mycoplasma pneumoniae by loop-mediated isothermal amplification, *Kansenshogaku Zasshi*, vol. 82, No. 3, pp. 168-176, 2008 (Abstract, 2 pages).

Zhao et al., "Detection of *Mycoplasma pneumoniae* by Colorimetric Loop-Mediated Isothermal Amplification," *Acta Microbiologica et Immunologica Hungarica*, vol. 60, No. 1, pp. 1-9, 2013.

* cited by examiner

SEQUENCE LISTING

<160> NUMBER OF SEQ ID NOS: 6

<210> SEQ ID NO 1
<211> LENGTH: 1779
<212> TYPE: DNA
<213> ORGANISM: Mycoplasma pneumoniae

<400> SEQUENCE: 1

```
atgccaaatc ctgttagatt tgtttaccgt gttgatttga gaagccctga agaaattttt      60
gaacatggct tttcaacttt aggtgatgtg agaaatttct ttgaacacat tctctccact     120
aattttggta gaagctatt tatttccact tcagaaacac ccacagcagc tattcgcttc     180
tttggtagct ggttacggga atatgtacca gagcacccca gaagggctta cttatatgaa     240
attcgtgccg accaacactt ttacaatgcc cgcgccactg gggagaactt gttagattta     300
atgcgtcaaa gacaagtagt atttgactct ggtgatcgag aaatggcaca aatgggaatt     360
agagctttac gcacttcctt tgcgtatcaa cgtgaatggt ttaccgatgg tccaattgca     420
gcagctaatg tccgtagtgc ttgactagta gatgctgttc ccgttgaacc tggtcatgct     480
caccacccgg ctggtcgtgt tgtagagact actagaatta atgaaccgga aatgcacaac     540
cctcattatc aagagctgca aacccaagcc aatgatcaac catgattgcc aacaccagga     600
atagctactc ctgtacattt atcaattccc caagcagctt ccgttgctga tgtttcggaa     660
ggtacttccg cttcgctatc gtttgcgtgc cctgattgaa gtccaccttc tagtaatggt     720
gaaaatccgc tagacaaatg cattgcggaa aagattgata actataacct acaatcctta     780
ccacagtacg ctagcagtgt aaaggaactg gaagatacac cagtatacct aaggggaatt     840
aaaacgcaaa aaacctttat gttacaagca gatccgcaaa ataacaatgt cttttttggtc     900
gaagtaaacc ccaaacaaaa gtccagcttt ccccaaacca tcttcttttg ggatgtttat     960
caacgaattt gtctcaagga tttaactggt gcacaaatca gtctttcgct tactgccttt    1020
actactcagt atgctggtca gctcaaagtg caccttagtg ttagcgcggt taatgccgtg    1080
aaccaaaagt gaaaaatgac accgcaagac attgcaataa ctcagtttcg ggtctcctct    1140
gaactgttag gtcaaactga aaatggcttg ttctgaaata ccaagagtgg tggttcacaa    1200
cacgatttgt atgtatgtcc tttgaaaaat ccacctagtg atttggaaga attacaaata    1260
attgttgatg aatgtactac ccatgcgcag tttgttacta tgcgtgcagc tagcaccttc    1320
tttgttgatg ttcagctagg ctggtattga agggttatt actataccc acaattaagt    1380
ggttgatctt atcagatgaa aacaccagat ggacagatat tctatgatct aaaaacttcg    1440
aaaatcttct tgtccagga caaccaaaac gtgttctttc tccataataa actcaacaaa    1500
caaactggtt acagctggga ttgagtagaa tggctaaaac atgacatgaa tgaggacaaa    1560
gacgaaaact ttaaatggta cttttcgcgt gatgaccttt ccattccttc cgttgaaggg    1620
cttaacttcc gccacattcg ctgttacgct gacaaccagc agttaaaggt gatcataagc    1680
ggttcacgtt ggggcggttg gtactccact tacgataaag ttgaaagtaa tgtcgaagat    1740
aagatttttgg tcaaagatgg ttttgatcgc ttttagcga                          1779
```

<210> SEQ ID NO 2

```
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
ccacctagtg atttggaaga                                              20

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 3
ggacaaagaa gattttcgaa gtt                                          23

<210> SEQ ID NO 4
<211> LENGTH: 47
<212> TYPE: DNA
<213> ORGANISM: Artificial Sequence
<220> FEATURE:
<223> OTHER INFORMATION: Synthetic oligonucleotide primer

<400> SEQUENCE: 4
gctgaacatc aacaaagaag gtgcattgtt gatgaatgta ctaccca                47

<210> SEQ ID NO 5
<211> LENGTH: 47
<212> TYPE: DNA
<213> ORGANISM: Artificial Sequence
<220> FEATURE:
<223> OTHER INFORMATION: Synthetic oligonucleotide primer

<400> SEQUENCE: 5
atacccacaa attaagtggt tgattcatag aatatctgtc catctgg                47

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
ctgcacgcat agtaacaaac tg                                           22
```

METHODS AND COMPOSITIONS FOR ISOTHERMAL AMPLIFICATION AND DETECTION OF MYCOPLASMA PNEUMONIAE

CROSS REFERENCE TO RELATED APPLICATIONS

This application claims the benefit of U.S. Provisional Application No. 62/116,166, filed on Feb. 13, 2015, which is incorporated herein by reference in its entirety.

FIELD

This disclosure relates to *Mycoplasma pneumoniae*, particularly methods and compositions for amplifying or detecting *M. pneumoniae* nucleic acids.

BACKGROUND

*Mycoplasma pneumoniae* is a leading cause of community-acquired pneumonia across all ages and patient populations, in all climates and seasons, and epidemics are seen about every 3-7 years. It is difficult to distinguish *M. pneumoniae* infection from other respiratory pathogens based upon clinical presentation. This promotes use of potentially inappropriate antibiotics, which can lead to development of microbial resistance. In addition, delayed recognition of outbreaks results in continued spread in households and the larger community.

Current methods for diagnosing *M. pneumoniae* infection include culture, serology, or PCR. However, these methods require time (hours to days), multiple samples, and/or specialized equipment and expensive reagents. In addition, these types of methods are not suitable for use at point-of-care. Thus, there remains a need for development of specific, sensitive, rapid, and inexpensive methods for diagnosis of *M. pneumoniae* infection, particularly at the point-of-care.

SUMMARY

Disclosed herein are methods and compositions (e.g., oligonucleotide primers) for isothermal amplification and detection of *M. pneumoniae* nucleic acids in a sample. In some examples, detection of *M. pneumoniae* in a sample (such as a sample from a subject) indicates that the subject is infected with *M. pneumoniae*, which is a causative agent of community-acquired pneumonia. In some examples, the subject may be symptomatic or asymptomatic (e.g., a carrier).

In some embodiments, the methods include contacting a sample with a set of LAMP primers specific for a *M. pneumoniae* CARDS toxin-encoding nucleic acid under conditions sufficient to produce an *M. pneumoniae* nucleic acid amplification product and detecting the resulting *M. pneumoniae* amplification product. In particular examples, the set of LAMP primers includes two or more primers (such as 2, 3, or 4 primers) with a nucleic acid sequence at least 95% identical to any one of SEQ ID NOs: 2-5. The set of LAMP primers optionally further includes a primer with a nucleic acid sequence at least 95% identical to SEQ ID NO: 6. In some embodiments, the methods further include contacting the sample with a fluorescent indicator dye (such as calcein). The reaction buffer utilized in the disclosed methods in some examples includes $Mg^{2+}$ and $Mn^{2+}$ at a ratio of about 4:1.

Kits including sets of LAMP primers for detection of *M. pneumoniae* CARDS toxin nucleic acids (such as SEQ ID NOs: 2-5 or SEQ ID NOs: 2-6) are provided herein. In particular examples, the kits also include a fluorescent indicator dye (such as calcein) and/or a buffer including $Mg^{2+}$ and $Mn^{2+}$ at a ratio of about 4:1.

The foregoing and other features of the disclosure will become more apparent from the following detailed description, which proceeds with reference to the accompanying figures.

BRIEF DESCRIPTION OF THE DRAWINGS

FIGS. 3A and 3B show analytical sensitivity of the *M. pneumoniae* CARDS toxin LAMP assay.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Feb. 4, 2016, and is 3955 bytes, which is incorporated by reference herein.

SEQ ID NO: 1 is the nucleic acid sequence of an exemplary *M. pneumoniae* CARDS toxin gene.

SEQ ID NOs: 2-6 are nucleic acid sequences of exemplary *M. pneumoniae* LAMP primers.

DETAILED DESCRIPTION

I. Terms

Unless otherwise noted, technical terms are used according to conventional usage. Definitions of common terms in molecular biology may be found in *Lewin's Genes X*, ed. Krebs et al, Jones and Bartlett Publishers, 2009 (ISBN 0763766321); Kendrew et al. (eds.), *The Encyclopedia of Molecular Biology*, Blackwell Publishers, 1994 (ISBN 0632021829); Robert A. Meyers (ed.), *Molecular Biology and Biotechnology: a Comprehensive Desk Reference*, Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. mentioned herein are incorporated by reference in their entirety as were present on Feb. 13, 2015. In case of conflict, the present specification, including explanations of terms, will control.

Although methods and materials similar or equivalent to those described herein can be used to practice or test the disclosed technology, suitable methods and materials are described below. The materials, methods, and examples are illustrative only and are not intended to be limiting.

In order to facilitate review of the various embodiments of this disclosure, the following explanations of specific terms are provided:

Amplification: Increasing the number of copies of a nucleic acid molecule, such as a gene or fragment of a gene, for example at least a portion of an *M. pneumoniae* nucleic acid molecule. The products of an amplification reaction are called amplification products. An example of in vitro amplification is the polymerase chain reaction (PCR), in which a sample (such as a biological sample from a subject) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include real-time PCR, quantitative real-time PCR (qPCR), reverse transcription PCR (RT-PCR), quantitative RT-PCR (qRT-PCR), loop-mediated isothermal amplification (LAMP; see Notomi et al., *Nucl. Acids Res.* 28:e63, 2000); reverse-transcription LAMP (RT-LAMP); strand displacement amplification (see U.S. Pat. No. 5,744,311); transcription-mediated amplification (U.S. Pat. No. 5,399,491) transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Conditions sufficient for: Any environment that permits the desired activity, for example, that permits specific binding or hybridization between two nucleic acid molecules or that permits amplification and/or detection of a nucleic acid. Such an environment may include, but is not limited to, particular incubation conditions (such as time and/or temperature) or presence and/or concentration of particular factors, for example in a solution (such as buffer(s), salt(s), metal ion(s), detergent(s), nucleotide(s), enzyme(s), and so on).

Contact: Placement in direct physical association; for example in solid and/or liquid form. For example, contacting can occur in vitro with one or more primers and/or probes and a biological sample (such as a sample including nucleic acids) in solution.

Detectable label: A compound or composition that is conjugated (e.g., covalently linked) directly or indirectly to another molecule (such as a nucleic acid molecule) to facilitate detection of that molecule. Specific non-limiting examples of labels include fluorescent and fluorogenic moieties (e.g., fluorophores), chromogenic moieties, haptens (such as biotin, digoxigenin, and fluorescein), affinity tags, and radioactive isotopes (such as $^{32}$P, $^{33}$P, $^{35}$S, and $^{125}$I). The label can be directly detectable (e.g., optically detectable) or indirectly detectable (for example, via interaction with one or more additional molecules that are in turn detectable). Methods for labeling nucleic acids, and guidance in the choice of labels useful for various purposes, are discussed, e.g., in Green and Sambrook, *Molecular Cloning: A Laboratory Manual*, Cold Spring Harbor Laboratory Press, Fourth Edition, 2012, and Ausubel et al., *Short Protocols in Molecular Biology*, Current Protocols, Fifth Edition, 2002.

Fluorescent indicator dye: A fluorescent compound that responds to changes in environmental conditions (such as pH or metal ion concentration) by changes in fluorescence properties. In some examples, fluorescence of a fluorescent indicator dye is increased by a stimulus, such as binding of a metal ion. In other examples, fluorescence of a fluorescent indicator dye is decreased (quenched) by a stimulus, such as binding of a metal ion. The fluorescent indicator dye can be detected by any suitable method, including visually (e.g., under ambient or ultraviolet light) or using instrumentation for detection of fluorescence (such as a fluorimeter or real-time PCR system).

An exemplary, non-limiting, fluorescent indicator dye is calcein. The fluorescence of calcein is quenched by binding of $Mn^{2+}$; its fluorescence increases when $Mn^{2+}$ is not bound, or when $Mg^{2+}$ is bound. Additional Mg2+-sensitive fluorescent indicators include hydroxynaphthol blue, Mag-Fura-2 and Magnesium Green (Life Technologies, Grand Island, N.Y.) and Fluo-2 Mg, Fura-2 Mg, Indo-1 Mg, and Asante Magnesium Green (TEF Labs, Austin, Tex.). In some examples, fluorescence from the fluorescent indicator dyes useful in the methods disclosed herein is visibly detectable (for example, by eye, such as a colorimetric reagent), while in other examples, the fluorescence is detectable using an instrument, such as a fluorimeter or real-time PCR platform.

Isolated: An "isolated" biological component (such as a nucleic acid) has been substantially separated or purified away from biological or other components (for example biological components with which the component naturally occurs, such as chromosomal and extrachromosomal DNA, RNA, and proteins). Nucleic acids that have been "isolated" include nucleic acids purified by standard purification methods. The term also embraces nucleic acids prepared by recombinant expression in a host cell and subsequently purified, as well as chemically synthesized nucleic acid molecules. Isolated does not require absolute purity, and can include nucleic acid molecules that are at least 50% isolated, such as at least 75%, 80%, 90%, 95%, 98%, 99%, or even 99.9% isolated. An isolated nucleic acid may be in solution (e.g., water or an aqueous solution) or dried.

Isothermal amplification: Nucleic acid amplification that is not dependent on significant changes in temperature (in contrast to PCR, for example). Thus, it is carried out substantially at about the same single temperature. In some examples, isothermal amplification is substantially isothermal, for example, may include small variations in temperature, such as changes in temperature of no more than about 1-2° C. during the amplification reaction.

Loop-mediated isothermal amplification (LAMP): A method for amplifying DNA. The method is a single-step amplification reaction utilizing a DNA polymerase with strand displacement activity (e.g., Notomi et al., *Nucl. Acids. Res.* 28:E63, 2000; Nagamine et al., *Mol. Cell. Probes* 16:223-229, 2002; Mori et al., *J. Biochem. Biophys. Methods* 59:145-157, 2004). At least four primers, which are specific for eight regions within a target nucleic acid sequence, are typically used for LAMP; however, in some examples, two primers may be used for LAMP. The primers include a forward outer primer (F3), a backward outer primer (B3), a forward inner primer (FIP), and a backward inner primer (BIP). A forward loop primer (Loop F), and/or a backward loop primer (Loop B) can also be included in some embodiments. The amplification reaction produces a stem-loop DNA with inverted repeats of the target nucleic acid sequence. Reverse transcriptase can be added to the reaction for amplification of RNA target sequences. This variation is referred to as RT-LAMP.

*Mycoplasma pneumoniae*: A bacterium that causes respiratory disease (such as pneumonia) in humans. *M. pneumoniae* is responsible for about 15-20% of cases if atypical community acquired pneumonia. Multiple strains of *M. pneumoniae* have been identified, such as M129 and FH. Nucleic acid and protein sequences for *M. pneumoniae* are publicly available. For example, GenBank Accession No. NC_000912 (incorporated by reference as present in GenBank on Feb. 13, 2015) provides an exemplary *M. pneumoniae* genome sequence.

The *M. pneumoniae* CARDS toxin (community acquired respiratory distress syndrome toxin) is an ADP-ribosyltransferase that has been identified as a potential virulence factor in *M. pneumoniae* (Kannan and Baseman, Proc. Natl. Acad. Sci. USA 103:6724-6729, 2006). An exemplary *M. pneumoniae* CARDS toxin nucleic acid sequence is found at GenBank Accession No. DQ447750:

(SEQ ID NO: 1)
ATGCCAAATCCTGTTAGATTTGTTTACCGTGTTGATTTGAGAAGCCCT

GAAGAAATTTTTGAACATGGCTTTTCAACTTTAGGTGATGTGAGAAA

TTTCTTTGAACACATTCTCTCCACTAATTTTGGTAGAAGCTATTTTATT

TCCACTTCAGAAACACCCACAGCAGCTATTCGCTTCTTTGGTAGCTGG

TTACGGGAATATGTACCAGAGCACCCCAGAAGGGCTTACTTATATGA

AATTCGTGCCGACCAACACTTTTACAATGCCCGCGCCACTGGGGAGA

ACTTGTTAGATTTAATGCGTCAAAGACAAGTAGTATTTGACTCTGGT

GATCGAGAAATGGCACAAATGGGAATTAGAGCTTTACGCACTTCCTT

TGCGTATCAACGTGAATGGTTTACCGATGGTCCAATTGCAGCAGCTA

ATGTCCGTAGTGCTTGACTAGTAGATGCTGTTCCCGTTGAACCTGGTC

ATGCTCACCACCCGGCTGGTCGTGTTGTAGAGACTACTAGAATTAAT

GAACCGGAAATGCACAACCCTCATTATCAAGAGCTGCAAACCCAAG

-continued
CCAATGATCAACCATGATTGCCAACACCAGGAATAGCTACTCCTGTA

CATTTATCAATTCCCCAAGCAGCTTCCGTTGCTGATGTTTCGGAAGGT

ACTTCCGCTTCGCTATCGTTTGCGTGCCCTGATTGAAGTCCACCTTCT

AGTAATGGTGAAAATCCGCTAGACAAATGCATTGCGGAAAAGATTG

ATAACTATAACCTACAATCCTTACCACAGTACGCTAGCAGTGTAAAG

GAACTGGAAGATACACCAGTATACCTAAGGGGAATTAAAACGCAAA

AAACCTTTATGTTACAAGCAGATCCGCAAAATAACAATGTCTTTTTG

GTCGAAGTAAACCCCAAACAAAAGTCCAGCTTTCCCCAAACCATCTT

CTTTTGGGATGTTTATCAACGAATTTGTCTCAAGGATTTAACTGGTGC

ACAAATCAGTCTTTCGCTTACTGCCTTTACTACTCAGTATGCTGGTCA

GCTCAAAGTGCACCTTAGTGTTAGCGCGGTTAATGCCGTGAACCAAA

AGTGAAAAATGACACCGCAAGACATTGCAATAACTCAGTTTCGGGTC

TCCTCTGAACTGTTAGGTCAAACTGAAAATGGCTTGTTCTGAAATAC

CAAGAGTGGTGGTTCACAACACGATTTGTATGTATGTCCTTTGAAAA

ATCCACCTAGTGATTTGGAAGAATTACAAATAATTGTTGATGAATGT

ACTACCCATGCGCAGTTTGTTACTATGCGTGCAGCTAGCACCTTCTTT

GTTGATGTTCAGCTAGGCTGGTATTGAAGGGGTTATTACTATACCCC

ACAATTAAGTGGTTGATCTTATCAGATGAAAACACCAGATGGACAGA

TATTCTATGATCTAAAAACTTCGAAAATCTTCTTTGTCCAGGACAACC

AAAACGTGTTCTTTCTCCATAATAAACTCAACAAACAAACTGGTTAC

AGCTGGGATTGAGTAGAATGGCTAAAACATGACATGAATGAGGACA

AAGACGAAAACTTTAAATGGTACTTTTCGCGTGATGACCTTACCATT

CCTTCCGTTGAAGGGCTTAACTTCCGCCACATTCGCTGTTACGCTGAC

AACCAGCAGTTAAAGGTGATCATAAGCGGTTCACGTTGGGGCGGTTG

GTACTCCACTTACGATAAAGTTGAAAGTAATGTCGAAGATAAGATTT

TGGTCAAAGATGGTTTTGATCGCTTTTAGCGA

GenBank Accession Nos. DQ447746, DQ447747, DQ447748, and DQ447749 provide further exemplary *M. pneumoniae* CARDS toxin nucleic acid sequences, all of which are incorporated by reference herein as present in GenBank on Feb. 13, 2015.

Primer: Primers are short nucleic acids, generally DNA oligonucleotides 10 nucleotides or more in length (such as 10-60, 15-50, 20-40, 20-50, 25-50, or 30-60 nucleotides in length). Primers may be annealed to a complementary target DNA strand by nucleic acid hybridization to form a hybrid between the primer and the target DNA strand, and then extended along the target DNA strand by a DNA polymerase enzyme. Primer pairs or set of primers (such as 2, 3, 4, 5, 6, or more primers) can be used for amplification of a target nucleic acid, e.g., by PCR, LAMP, RT-LAMP, or other nucleic acid amplification methods known in the art.

Probe: A probe typically comprises an isolated nucleic acid (for example, at least 10 or more nucleotides in length, such as 10-60, 15-50, 20-40, 20-50, 25-50, or 30-60 nucleotides in length) with an attached detectable label or reporter molecule. Exemplary labels include radioactive isotopes, ligands, haptens, chemiluminescent agents, fluorescent molecules (e.g., fluorophores), and enzymes. Methods for labeling oligonucleotides and guidance in the choice of labels appropriate for various purposes are discussed, e.g., in Green and Sambrook, *Molecular Cloning: A Laboratory Manual*, Cold Spring Harbor Laboratory Press, Fourth Edition, 2012, and Ausubel et al., *Short Protocols in Molecular Biology*, Current Protocols, Fifth Edition, 2002.

Recombinant nucleic acid: A nucleic acid molecule that is not naturally occurring or has a sequence that is made by an artificial combination of two otherwise separated segments of nucleotide sequence. This artificial combination is accomplished by chemical synthesis or by the artificial manipulation of isolated segments of nucleic acids, e.g., by genetic engineering techniques such as those described in Sambrook and Russell, in *Molecular Cloning: A Laboratory Manual*, $3^{rd}$ Ed., Cold Spring Harbor Laboratory Press (2001). The term "recombinant" includes nucleic acids that have been altered solely by addition, substitution, or deletion of a portion of a natural nucleic acid molecule. A recombinant nucleic acid also includes a heterologous nucleic acid that is inserted in a vector. A "heterologous nucleic acid" refers to a nucleic acid that originates from a different genetic source or species, for example an *M. pneumoniae* nucleic acid inserted in a plasmid from another bacterial species (such as *E. coli*).

Sample (or biological sample): A specimen containing DNA (for example, genomic DNA or cDNA), RNA (including mRNA), protein, or combinations thereof. Examples include, but are not limited to isolated nucleic acids, cells, cell lysates, chromosomal preparations, tissues, and bodily fluids (such as blood, derivatives and fractions of blood (such as serum)), extracted galls, biopsied or surgically removed tissue (including tissues that are, for example, unfixed, frozen, fixed in formalin and/or embedded in paraffin), autopsy material, tears, milk, skin scrapes, surface washings, urine, sputum, cerebrospinal fluid, prostate fluid, pus, bone marrow aspirates, middle ear fluids, bronchoalveolar lavage, tracheal aspirates, nasopharyngeal swabs or aspirates, oropharyngeal swabs or aspirates, nasal washings, or saliva. In one example, a sample includes bacterial nucleic acids, for example, *M. pneumoniae* DNA. In particular examples, samples are used directly (e.g., fresh or frozen), or can be manipulated prior to use, for example, by extraction (for example of nucleic acids), fixation (e.g., using formalin) and/or embedding in wax (such as FFPE tissue samples).

Subject: Any multi-cellular vertebrate organism, such as human and non-human mammals (including non-human primates). In one example, a subject is known to be or is suspected of being infected with *M. pneumoniae*.

II. Methods of Detecting *M. pneumoniae* Nucleic Acids

Disclosed herein are methods of detecting *M. pneumoniae* nucleic acids in a sample (such as from a sample from a subject infected with or suspected to be infected with *M. pneumoniae*). The disclosed methods can be used to diagnose an infection with *M. pneumoniae* in a subject, for example, by analyzing a biological sample from the subject to detect *M. pneumoniae* nucleic acids in the sample. The disclosed methods can also be used to detect *M. pneumoniae* carriage in a subject, for example, presence of *M. pneumoniae* in the upper respiratory tract without symptomatic respiratory tract infection. In some examples, the methods include LAMP assays.

The methods described herein may be used for any purpose for which detection of *M. pneumoniae* nucleic acids is desirable, including diagnostic and prognostic applications, such as in laboratory and/or clinical settings. Appropriate samples include any conventional biological samples, including clinical samples obtained from a human or veterinary subject. Suitable samples include all biological samples useful for detection of infection in subjects, including, but not limited to, cells (such as buccal cells or peripheral blood mononuclear cells), tissues, autopsy samples, bone marrow aspirates, bodily fluids (for example, bronchoalveolar lavage (BAL), tracheal aspirates, sputum, oral fluids, nasopharyngeal (NP) swabs or aspirates, oropharyngeal (OP) swabs or aspirates, blood, serum, plasma, urine, cerebrospinal fluid, middle ear fluids, breast milk, or saliva), oral swabs, eye swabs, cervical swabs, vaginal swabs, rectal swabs, stool, and stool suspensions. The sample can be used directly or can be processed, such as by adding solvents, preservatives, buffers, or other compounds or substances. In some examples, nucleic acids are isolated from the sample. In other examples, isolation of nucleic acids from the sample is not necessary prior to use in the methods disclosed herein and the sample (such as a NP swabs, OP swabs, BAL, sputum, or other respiratory secretions) is used directly or with minimal pre-processing. For example, samples can be vortexed or diluted in water or buffer and used in the disclosed LAMP assays without additional processing. In some examples, the sample (for example, a sample containing cells) is pre-treated to lyse cells (for example with a lysis buffer, such as a buffer including detergent, and/or by thermal treatment, such as 10 minutes at about 95-98° C.).

Samples also include isolated nucleic acids, such as DNA, cDNA, RNA, or mRNA isolated from a biological specimen from a subject, an *M. pneumoniae* isolate, or other source of nucleic acids. Methods for extracting nucleic acids such as RNA and/or DNA from a sample are known to one of skill in the art; such methods will depend upon, for example, the type of sample in which the nucleic acid is found. Nucleic acids can be extracted using standard methods. For instance, rapid nucleic acid preparation can be performed using a commercially available kit (such as kits and/or instruments from Qiagen (such as DNEASY® or RNEASY® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987).

The disclosed methods are highly sensitive and/or specific for detection of *M. pneumoniae* nucleic acids. In some examples, the disclosed methods detect presence of at least 10 fg of *M. pneumoniae* nucleic acid (for example at least 100 fg, at least 1 pg, at least 10 pg, at least 100 pg, at least 1 ng, or more *M. pneumoniae* nucleic acid) in a sample or a particular reaction volume (such as per 25 µl reaction). In some examples, the disclosed methods detect about 10 fg to 1 µg *M. pneumoniae* nucleic acid per reaction (such as about 10 fg-1 pg, about 10 fg-100 fg, about 100 fg-10 pg, about 500 pg-100 ng, about 1 pg-1 about 1 pg-1 ng, about 10 pg-100 pg, about 100 pg-100 ng, or about 500 pg-10 ng). In particular, non-limiting examples, the disclosed methods have a limit of detection of about 10-100 fg. In other examples, the disclosed methods detect presence of genome equivalents of 1, 5, 10, 20, 50, 100, 1000, or more bacteria. One of skill in the art will recognize that the limit of detection of an assay depends on many factors (such as reaction conditions; amount, type, and quality of starting material; detection method utilized; and so on). The limit of detection using particular LAMP primer sets, such as those disclosed herein, may be even lower with modifications to the assay conditions, detection methods, or other parameters.

In some examples, the disclosed methods can predict with a sensitivity of at least 85% and/or a specificity of at least 85% for presence of an *M. pneumoniae* nucleic acid (such as an *M. pneumoniae* CARDS toxin nucleic acid), such as a sensitivity of at least 85%, 86%, 87%, 88%, 89%, 90%, 91%, 92%, 93%, 94%, 95%, 96%, 97%, 98%, 99%, or even 100% and/or a specificity of at least of at least 85%, 86%, 87%, 88%, 89%, 90%, 91%, 92%, 93%, 94%, 95%, 96%, 97%, 98%, 99%, or even 100%. In particular examples, the sensitivity of the disclosed methods is at least 85% (e.g., at least 90%, at least 95%, or at least 99%), for example when compared to a qPCR assay (e.g., an assay described in WO 2011/133433 or Winchell et al., *J. Clin. Microbiol.* 46:3116-3118, 2008). In some examples, the sensitivity of the disclosed assay is determined with respect to qPCR samples with a $C_t$ value less than 30 (see, e.g., Example 2, below).

Disclosed herein are methods for detecting *M. pneumoniae* nucleic acids in a sample, utilizing LAMP methods of amplification and detection. LAMP, which was first described by Notomi et al. (*Nucl. Acids Res.* 28:e63, 2000), is a one-step isothermal amplification method that can produce amplified nucleic acids in a short period of time using a DNA polymerase with strand displacement activity. The isothermal nature of LAMP allows for assay flexibility because it can be used with simple and inexpensive heating devices, which can facilitate *M. pneumoniae* detection in settings other than centralized clinical laboratories, including at the point-of-care (POC).

In some examples, LAMP (or RT-LAMP) assays can be multiplexed through the addition of multiple LAMP primer sets with different specificities. This capability is advantageous, for example, because it allows for incorporation of internal control(s), amplification of two or more regions within the same target, or detection of two or more targets (e.g., two or more targets in the same pathogen or two or more pathogens) in a single reaction. In some examples, the disclosed methods include a multiplex LAMP or RT-LAMP assay for detection of *M. pneumoniae* (for example, utilizing a set of *M. pneumoniae* LAMP primers disclosed herein) in combination with one or more sets of LAMP primers specific for additional pathogens, including but not limited to one or more of *Chlamydophila pneumoniae, Streptococcus pneumoniae, Legionella*, and other bacterial or viral pathogens. In particular examples, the multiplex LAMP assay includes LAMP primers specific for *S. pneumoniae* (as disclosed herein) and one or more other respiratory pathogens.

In some embodiments, the methods include contacting a sample (such as a sample from a subject) with at least one set of LAMP primers, such as a set of LAMP primers specific for an *M. pneumoniae* nucleic acid (for example, a set of primers specific for an *M. pneumoniae* CARDS toxin nucleic acid) under conditions sufficient for amplification of the *M. pneumoniae* nucleic acid, thereby producing an amplification product. In some embodiments, the methods include amplifying an *M. pneumoniae* nucleic acid having at least 90% sequence identity (such as at least 95%, 98%, or more sequence identity) to an *M. pneumoniae* CARDS toxin nucleic acid (e.g. SEQ ID NO: 1), or a portion thereof. In some examples, the methods include amplifying an *M. pneumoniae* nucleic acid encompassed by nucleotides 1231-1533 of SEQ ID NO: 1 or a nucleic acid having at least about 95% identity to a nucleic acid encompassed by nucleotides 1231-1533 of SEQ ID NO: 1.

In some embodiments, the methods include contacting the sample with a set of LAMP primers including 2 or more (such as 2, 3, or 4) of a forward outer primer (F3), a backward outer primer (B3), a forward inner primer (FIP), and a backward inner primer (BIP) specific for an *M. pneumoniae* CARDS toxin nucleic acid. In some examples, the set of LAMP primers includes at least an FIP primer (such as SEQ ID NO: 4), and a BIP primer (such as SEQ ID NO: 5). In other examples, the set of LAMP primers includes at least an F3 primer (such as SEQ ID NO: 2), a B3 primer (such as SEQ ID NO: 3), an FIP primer (such as SEQ ID NO: 4), and a BIP primer (such as SEQ ID NO: 5). In additional embodiments, the set of LAMP primers further includes one or more of a forward loop primer and a backward loop primer. For example, the set of LAMP primers may further include a forward loop primer (such as SEQ ID NO: 6).

An exemplary set of LAMP primers for amplification of an *M. pneumoniae* CARDS toxin nucleic acid includes an F3 primer including a nucleic acid with at least 90% (for example, at least 95%, 98%, or more) sequence identity to SEQ ID NO: 2, a B3 primer including a nucleic acid with at least 90% (for example, at least 95%, 98%, or more) sequence identity to SEQ ID NO: 3, an FIP primer including a nucleic acid with at least 90% (for example, at least 95%, 98%, or more) sequence identity to SEQ ID NO: 4, and a BIP primer including a nucleic acid with at least 90% (for example, at least 95%, 98%, or more) sequence identity to SEQ ID NO: 5, and optionally including a Loop F primer including a nucleic acid with at least 90% (for example, at least 95%, 98%, or more) sequence identity to SEQ ID NO: 6, or the reverse complement of any of the disclosed primers. In one example, the sample is contacted with a set of LAMP primers for amplifying an *M. pneumoniae* CARDS toxin nucleic acid comprising, consisting essentially of, or consisting of the nucleic acid sequence of each of SEQ ID NOs: 2-5 under conditions sufficient to amplify a CARDS toxin nucleic acid. In another example, the sample is contacted with a set of LAMP primers for amplifying an *M. pneumoniae* CARDS toxin nucleic acid includes primers comprising, consisting essentially of, or consisting of the nucleic acid sequence of each of SEQ ID NOs: 2-6 under conditions sufficient to amplify a CARDS toxin nucleic acid.

The amplification product produced by the methods disclosed herein is detected by any suitable method, such as detection of turbidity, color, fluorescence, or by gel electrophoresis. The detection can be carried out "by eye" (e.g., visually observing changes in turbidity, color, or fluorescence under ambient or ultraviolet light) or using an appropriate instrument (e.g., a turbidometer, fluorimeter, or spectrophotometer). One of ordinary skill in the art can select appropriate detection techniques for the methods described herein. In one particular example, the methods include use of a fluorescent indicator dye (such as calcein) and amplification of an *M. pneumoniae* nucleic acid is detected visually (under ambient or ultraviolet light) or using fluorimetric detection.

The sample and the set of LAMP primers are contacted under conditions sufficient for amplification of an *M. pneumoniae* nucleic acid (such as an *M. pneumoniae* CARDS toxin nucleic acid). The sample is contacted with the set of LAMP primers at a concentration sufficient to support amplification of an *M. pneumoniae* nucleic acid. In some examples, the amount of each primer is about 0.1 μM to about 5 μM (such as about 0.2 μM to about 2 μM, or about 0.2 µM to about 1.6 µM). Each primer can be included at a different concentration, and appropriate concentrations for each primer can be selected by one of skill in the art using routine methods. Exemplary non-limiting primer concentrations are provided in Example 1, below.

In some examples, the LAMP reaction is carried out in a reaction mixture including a suitable buffer (such as a phosphate buffer or Tris buffer). The buffer may also include additional components, such as salts (such as KCl or NaCl, magnesium and/or manganese salts (e.g., $MgCl_2$, $MgSO_4$, $MnC_{12}$, and/or $MnSO_4$), and/or ammonium salts (e.g., $(NH_4)_2SO_4$)), detergents (e.g., TWEEN®-20, TRITON®-X100), or other additives (such as betaine or dimethylsulfoxide). One of skill in the art can select an appropriate buffer and any additives using routine methods. In one non-limiting example, the buffer includes 20 mM Tris-HCl, 10 mM $(NH_4)_2SO_4$, 50 mM KCl, 8 mM $MgSO_4$, 0.1% TRITON®-X100, and 0.8 M betaine. In another non-limiting example, the reaction buffer includes 20 mM Tris (pH 8.8), 10 mM KCl, 8 mM $MgSO_4$, 10 mM $(NH_4)_2SO_4$, 0.1% TWEEN®-20, 0.8 M betaine, and 0.5 mM $MnCl_2$. In some examples, the amount of $MgSO_4$ and $MnCl_2$ is adjusted to provide a 4:1 ratio of Mg:Mn, such as 5.5 mM $MgSO_4$, and 1.375 mM $MnCl_2$. Exemplary commercially available reaction buffers include 1× Isothermal Amplification Buffer (New England Biolabs, Ipswich, Mass.), LoopAmp Reaction Mix (Eiken Chemical Co., Ltd., Tokyo, Japan), and ILLUMIGENE reaction buffer (Meridian Bioscience, Inc., Cincinnati, Ohio). The buffer components and/or concentrations may be varied, for example, depending on the detection method utilized, as discussed below. The reaction mixture also includes nucleotides or nucleotide analogs. In some examples, an equimolar mixture of dATP, dCTP, dGTP, and dTTP (referred to as dNTPs) is included, for example about 0.5-2 mM dNTPs.

A DNA polymerase with strand displacement activity is also included in the reaction mixture. Exemplary DNA polymerases include Bst DNA polymerase, Bst 2.0 DNA polymerase, Bst 2.0 WarmStart™ DNA polymerase (New England Biolabs, Ipswich, Mass.), Phi29 DNA polymerase, Bsu DNA polymerase, OmniAmp™ DNA polymerase (Lucigen, Middleton, Mich.), Taq DNA polymerase, $Vent_R$® and Deep $Vent_R$® DNA polymerases (New England Biolabs), 9° $N_m$™ DNA polymerase (New England Biolabs), Klenow fragment of DNA polymerase I, PhiPRD1 DNA polymerase, phage M2 DNA polymerase, T4 DNA polymerase, and T5 DNA polymerase. In some examples, about 1 to 20 U (such as about 1 to 15 U, about 2 to 12 U, about 10 to 20 U, about 2 to 10 U, or about 5 to 10 U) of DNA polymerase is included in the reaction. In some examples, the polymerase has strand displacement activity and lacks 5'-3' exonuclease activity. In one non-limiting example, the DNA polymerase is Bst 2.0 DNA polymerase (New England Biolabs, Ipswich, Mass.), for example about 8 U Bst 2.0 DNA polymerase per reaction.

The reaction mixture, including sample, LAMP primers, buffers, nucleotides, DNA polymerase, and any other components, is incubated for a period of time and at a temperature sufficient for production of an amplification product. The reaction may be carried out under substantially isothermal conditions. In some examples, the reaction conditions include incubating the reaction mixture at about 37° C. to about 70° C. (such as about 40° C. to about 70° C., about 50° C. to about 65° C., about 60° C. to 65° C.), for example about 40° C., about 45° C., about 50° C., about 55° C., about 60° C., about 61° C., about 62° C., about 63° C., about 64° C., about 65° C., about 66° C., about 67° C., about 68° C., about 69° C., or about 70° C. The reaction mixture is incubated for at least about 5 minutes (such as about 10, about 15, about 20, about 30, about 40, about 50, about 60, about 70, about 80 about 90, about 100, about 110, about 120 minutes or more), for example about 10-120 minutes, about 15-90 minutes, about 20-70 minutes, or about 30-60 minutes. In one non-limiting example, the reaction conditions include incubating the reaction mixture at about 62° C. for about 60 minutes. In additional examples, the incubation is under substantially isothermal conditions, such as maintaining temperatures that are within 1-2° of one another. For example, the reaction can be incubated for 30-60 "cycles," such as cycles of 15 seconds at 62° C. and 45 seconds at 63° C. Such "cycles" may be used to maintain a substantially constant isothermal environment, for example if a thermocycler that does not allow a single incubation temperature is utilized in the method. The reaction can optionally be terminated by incubation for a short time at a higher temperature, for example about 2-10 minutes at about 80-95° C.

Following incubation of the reaction mixture under conditions sufficient for amplification of an *M. pneumoniae* nucleic acid, the amplification product is detected by any suitable method. The detection methods may be quantitative, semi-quantitative, or qualitative. Accumulation of an amplification product (for example, compared to a negative control, such as a reagent only (non-template) control) indicates presence of *M. pneumoniae* nucleic acids in the sample. In some examples, accumulation of an amplification product is detected by measuring the turbidity of the reaction mixture (for example, visually or with a turbidometer). In other examples, amplification product is detected using gel electrophoresis, for example by detecting presence or amount of amplification product with agarose gel electrophoresis. In some examples, amplification product is detected using a colorimetric assay, such as with an intercalating dye (for example, propidium iodide, SYBR green or PICOGREEN fluorescent dyes) or a chromogenic or colorimetric reagent (such as hydroxynaphthol blue, see, e.g., Goto et al., *BioTechniques* 46:167-172, 2009). In further examples, amplification product is detected by a fluorescent indicator dye such as calcein (see, e.g., Tomita et al., *Nat. Protoc.* 3:877-882, 2008, discussed further below) or hydroxynaphthol blue (also referred to as a colorimetric reagent herein). In some examples, the amplification product is detected in real-time, for example using an optical detection system, such as ABI 7500 Real-Time PCR system (Applied Biosystems/Life Technologies, Grand Island, N.Y.) or ESEQUANT fluorescence measurement system (Qiagen, Valencia, Calif.). In other examples, amplification products are detected using a detectable label incorporated in (e.g., is covalently attached to) one or more of the LAMP primers. The detectable label may be optically or visually detectable, for example, by eye or using a spectrophotometer or fluorimeter.

In particular embodiments, the disclosed methods include calcein in the reaction, which provides for fluorescent detection of the amplification product. In some examples, the reaction mixture includes calcein at a concentration of about 5 µM to about 50 µM (such as about 10-50 µM, about 15-40 µM, about 20-30 µM, or about 6-25 µM). In one non-limiting example, the reaction mixture includes about 25 µM calcein. Calcein is a fluorescence indicator dye that is quenched by manganese ions and has increased fluorescence when bound to magnesium ions. The LAMP assay produces large amounts of pyrophosphate, which strongly binds to metal ions (particularly manganese and magnesium) and forms an insoluble precipitate. Thus, in some examples, LAMP assays including calcein include both manganese (e.g., $MnCl_2$ or $MnSO_4$) and magnesium (e.g., $MgCl_2$ or $MgSO_4$). As the amplification reaction proceeds, pyrophosphate is produced and competes with calcein for binding to $Mn^{2+}$. This reduces the quenching of the calcein, and also allows $Mg^{2+}$ to bind to the calcein, further increasing its fluorescence.

Figure 2A:
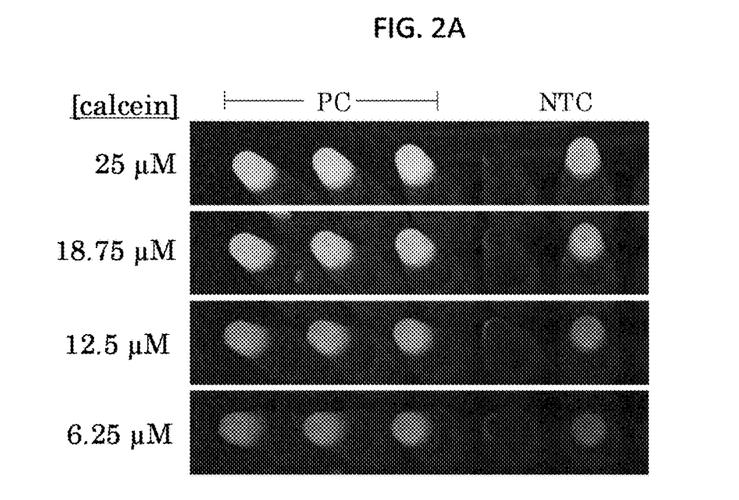
FIGS. 2A and 2B show visual readouts of *M. pneumoniae* LAMP assays with the indicated amounts of calcein (FIG. 2A) or 25 µM calcein and the indicated ratios of $Mg^{2+}:Mn^{2+}$ (FIG. 2B). PC, positive control (1 ng *M. pneumoniae* M129 nucleic acid); NTC, no template control.
Figure 2B:
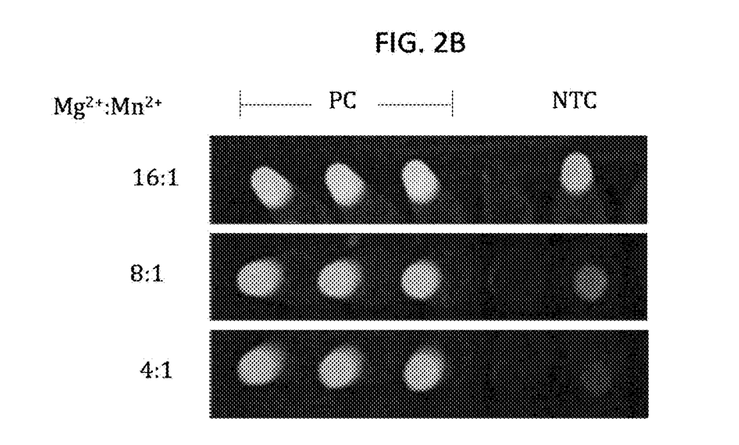

In the methods disclosed herein, a previously utilized ratio of $Mg^{2+}$ to $Mn^{2+}$ (16:1; see, e.g., Tomita et al., *Nature Protocols* 3:877-892, 2008) produced high levels of fluorescence in negative control samples (see Example 2 and FIGS. 2A and 2B). The inventors have surprisingly discovered that altering the ratio of $Mg^{2+}$ to $Mn^{2+}$ decreased the background fluorescence in LAMP assays, such as those utilizing LAMP primer sets including SEQ ID NOs: 2-5 or 2-6. Thus in particular examples, the methods described herein include in the reaction mixture calcein and a buffer including a ratio of $Mg^{2+}$ to $Mn^{2+}$ that is less than about 16:1 (such as less than 12:1, less than 10:1, less than 8:1, less than 4:1, or less than 2:1). In particular non-limiting examples, the ratio of $Mg^{2+}$ to $Mn^{2+}$ is about 8:1 or about 4:1.

III. Oligonucleotide Primers

Primers (such as isolated nucleic acid primers) suitable for use in the disclosed methods are described herein. In some examples, the primers are suitable for detection of *M. pneumoniae* nucleic acids using LAMP assays described herein. LAMP primer sets typically include a forward outer primer (F3), a backward outer primer (B3), a forward inner primer (FIP), and a backward inner primer (BIP). A forward loop primer (Loop F), and/or a backward loop primer (Loop B) can also be included in some embodiments. At least some of the LAMP primers are non-naturally occurring nucleic acid molecules, for example, have sequences that do not occur in nature. In particular, the FIP and BIP primers are composed of non-contiguous nucleic acid sequences, and include a portion complementary to a first strand of a double-strand nucleic acid and another portion complement to a second strand of a double-stranded nucleic acid (e.g., reverse complement of a first strand sequence)

In some embodiments, the disclosed primers are between 10 and 60 nucleotides in length (for example 15-50, 20-50, 30-60, or 25-40 nucleotides in length). In some examples, the primers are 10, 11, 12, 13, 14, 15, 16, 17, 18, 19, 20, 21, 22, 23, 24, 25, 26, 27, 28 29, 30, 31, 32, 32, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length and are capable of hybridizing to, and in some examples, amplifying the disclosed nucleic acid molecules. In some examples, the primers and/or probes are at least 10, 15, 20, 25, 30, 35, 40, 45, 50, 55, or 60 nucleotides in length. In other examples, the primers and/or probes may be no more than 10, 15, 20, 25, 30, 35, 40, 45, 50, 55, or 60 nucleotides in length.

In some examples, the disclosed primers include LAMP primers for amplification of *M. pneumoniae* nucleic acids, such as an *M. pneumoniae* CARDS toxin-encoding nucleic acid (for example SEQ ID NO: 1). The primers include nucleic acid sequences with at least 85% sequence identity (for example, at least 86%, 87%, 88%, 89%, 90%, 91%, 92%, 93%, 94%, 95%, 96%, 97%, 98%, 99%, or 100% identity) to CCACCTAGTGATTTGGAAGA (F3, SEQ ID NO: 2), GGACAAAGAAGATTTTCGAAGTT (B3, SEQ ID NO: 3), GCTGAACATCAACAAAGAAGGTGCATTGTTGATGAATGTACTACCCA (FIP, SEQ ID NO: 4), ATACCCCACAATTAAGTGGTTGATTCATA-GAATATCTGTCCATCTGG (BIP, SEQ ID NO: 5), and/or CTGCACGCATAGTAACAAACTG (Loop F, SEQ ID NO: 6).

In some examples, at least one of the primers includes a detectable label, such as a fluorophore, radiolabel, hapten (such as biotin), or chromogen. In some examples, a detectable label is attached (e.g., covalently or non-covalently attached) to an oligonucleotide. The attachment may be to any portion of the oligonucleotide, including to a base, sugar, phosphate backbone, or 5' or 3' end of the oligonucleotide. The label may be directly attached to the oligonucleotide or indirectly attached, for example through a linker molecule. In particular examples, a LAMP primer (e.g., one of SEQ ID NOs: 2-6) includes a fluorophore at the 5' or 3' end. In some examples, the fluorophore is HEX, FAM, TET, fluorescein, fluorescein isothiocyanate (FITC), or QFITC (XRITC). One of skill in the art can select additional suitable fluorophores (see, e.g., *The Molecular Probes Handbook*, Life Technologies, 11$^{th}$ Edition, 2010).

Although exemplary primer sequences are provided herein, the primer sequences can be varied slightly by moving the primer a few nucleotides upstream or downstream from the nucleotide positions that they hybridize to on the target nucleic molecule acid, provided that the probe and/or primer is still specific for the target nucleic acid sequence. For example, variations of the primers disclosed as SEQ ID NOs: 2-6 can be made by "sliding" the probes or primers a few nucleotides 5' or 3' from their positions, and such variations will still be specific for the respective target nucleic acid sequence.

Also provided by the present disclosure are primers that include variations to the nucleotide sequences shown in any of SEQ ID NOs: 2-6, as long as such variations permit detection of the target nucleic acid molecule. For example, a primer can have at least 85%% sequence identity such as at least 86%, 87%, 88%, 89%, 90%, 91%, 92%, 93%, 94%, 95%, 96%, 97%, 98%, or 99% identity to a nucleic acid including the sequence shown in any of SEQ ID NOs: 2-6. In such examples, the number of nucleotides does not change, but the nucleic acid sequence shown in any of SEQ ID NOs: 2-6 can vary at a few nucleotides, such as changes at 1, 2, 3, 4, 5, or 6 nucleotides.

The present application also provides primers that are slightly longer or shorter than the nucleotide sequences shown in any of SEQ ID NOs: 2-6, as long as such deletions or additions permit amplification and/or detection of the desired target nucleic acid molecule. For example, a primer can include a few nucleotide deletions or additions at the 5'- or 3'-end of the probe or primers shown in any of SEQ ID NOs: 2-6, such as addition or deletion of 1, 2, 3, 4, 5, or 6 nucleotides from the 5'- or 3'-end, or combinations thereof (such as a deletion from one end and an addition to the other end). In such examples, the number of nucleotides changes.

Also provided are primers that are degenerate at one or more positions (such as 1, 2, 3, 4, 5, or more positions), for example, a primer that includes a mixture of nucleotides (such as 2, 3, or 4 nucleotides) at a specified position in the primer. In other examples, the primers disclosed herein include one or more synthetic (e.g., non-naturally occurring) bases or alternative bases (such as inosine). In other examples, the primers disclosed herein include one or more modified nucleotides or nucleic acid analogues, such as one or more locked nucleic acids (see, e.g., U.S. Pat. No. 6,794,499), an altered sugar moiety, an inter-sugar linkage, a non-naturally occurring nucleotide linkage, a phosphorothioate oligodeoxynucleotide, a peptide nucleic acid (PNA), or one or more superbases (Nanogen, Inc., Bothell, Wash.).

IV. Kits

The nucleic acid primers disclosed herein can be supplied in the form of a kit, for example, for use in the detection or amplification of one or more *M. pneumoniae* nucleic acids. In such a kit, an appropriate amount of one or more of the nucleic acid primers (such as one or more of SEQ ID NOs: 2-6) are provided in one or more containers or in one or more individual wells of a multiwell plate or card. Nucleic acid primers may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid primers (for example, 1, 2, 3, 4, 5, 6, or more primers) for use in amplification and/or detection of *M. pneumoniae* nucleic acids.

One or more positive and/or negative control primers and/or nucleic acids also may be supplied in the kit. Exemplary negative controls include non-*M. pneumoniae* nucleic acids (such as human nucleic acids). Exemplary positive controls include purified *M. pneumoniae* nucleic acid or a vector or plasmid including the *M. pneumoniae* target sequence, as well as primers and nucleic acids for amplification of human target nucleic acids (such as human β-actin or RNaseP) or primers and nucleic acids for amplification of other bacterial target nucleic acids. One of skill in the art can select suitable positive and negative controls for the assays disclosed herein.

In some examples, one or more primers (such as one or more sets of primers), are provided in pre-measured single use amounts in individual, typically disposable, tubes, wells, plates, cards, or equivalent containers. In some examples, a set of primers (such as each of SEQ ID NOs: 2-5 or each of SEQ ID NOs: 2-6) is included in a single container. In this example, the sample to be tested for the presence of the target nucleic acids can be added to the individual container(s) and amplification and/or detection can be carried out directly. The kit may also include additional reagents for the detection and/or amplification of *M. pneumoniae* nucleic acids, such as buffer(s), nucleotides (such as dNTPs), enzymes (such as DNA polymerase and/or reverse transcriptase), or other suitable reagents. The additional reagents may be in separate container(s) from the one or more primers or may be included in the same container as the primer(s).

In some examples, the kit includes one or more compounds for detecting an amplification product, such as a DNA intercalator (e.g., propidium iodide, SYBR green or PICOGREEN fluorescent dyes) a chromogenic or colorimetric reagent (such as hydroxynaphthol blue), or a fluorescent indicator (such as calcein). In a particular example, the kit includes calcein and a buffer containing a ratio of $Mg^{2+}$ to $Mn^{2+}$ of less than 16:1, such as a ratio of $Mg^{2+}$ to $Mn^{2+}$ of about 8:1, about 4:1, or less.

In particular embodiments, the kits include at least one set of LAMP primers for amplification and/or detection of *M. pneumoniae* nucleic acids. In one example, the kit includes a set of primers comprising nucleic acid sequences at least 95% identical to each of SEQ ID NOs: 2-5, and optionally a primer comprising a nucleic acid sequence at least 95% identical to SEQ ID NO: 6. In some examples, the kit includes a set of LAMP primers including primers comprising or consisting of the nucleic acid sequence of each of SEQ ID NOs: 2-5, and optionally a primer comprising or consisting of the nucleic acid sequence of SEQ ID NO: 6.

The present disclosure is illustrated by the following non-limiting Examples.

Example 1

Design of LAMP Primers and Assay Conditions for *M. pneumoniae* Detection

This example describes the design and selection of primers for a LAMP assay for detecting *M. pneumoniae* and optimization of the assay for improved sensitivity.

LAMP primers were designed for amplification of a portion of the CARDS toxin gene of *M. pneumoniae* M129 (GenBank Accession No. DQ44750.1) using the EIKEN primer Explorer tool (available on the World Wide Web at primerexplorer.jp/e/). The parameters for the primer design are shown in Table 1.

TABLE 1

| LAMP primer design parameters | |
|---|---|
| Primer | $T_m$ (° C.) |
| F3 (forward displacement primer) | 56.1 |
| B3 (backward displacement primer) | 57.2 |
| FIP (forward inner primer) | F2 region 57.5 |
| | F1c region 62.8 |
| BIP (backward inner primer) | B2 region 56.6 |
| | B1c region 60.1 |
| FLP (forward loop primer) | 60.1 |

Five sets of primers (F3, B3, FIP, and BIP) were generated by the primer Explorer tool and were synthesized for testing. Total nucleic acid was extracted from 400 µl clinical specimens with MagNA Pure™ Compact system (Roche Diagnostics, Indianapolis, Ind.) according to the manufacturer's protocol and eluted into 100 µl. The LAMP reaction mix included 5 µl of extracted DNA in a 20 µl volume with LoopAmp kit reagents (Eiken Chemical Co., Ltd., Tokyo, Japan). Amplification was monitored in real-time on an ABI 7500 Fast PCR real-time PCR system (Applied Biosystems/Life Technologies, Grand Island, N.Y.). In some experiments, the reaction mix was as described in Tomita et al. (*Nature Protoc.* 3:877-882, 2008), except that the concentrations of $MgCl_2$ and $MnCl_2$ were adjusted as described below. Primers were used at 0.2 µM each for F3 and B3, 1.6 µM each for FIP and BIP, and 0.8 µM FLP, with 8 U of Bst 2.0 polymerase.

Figure 1:
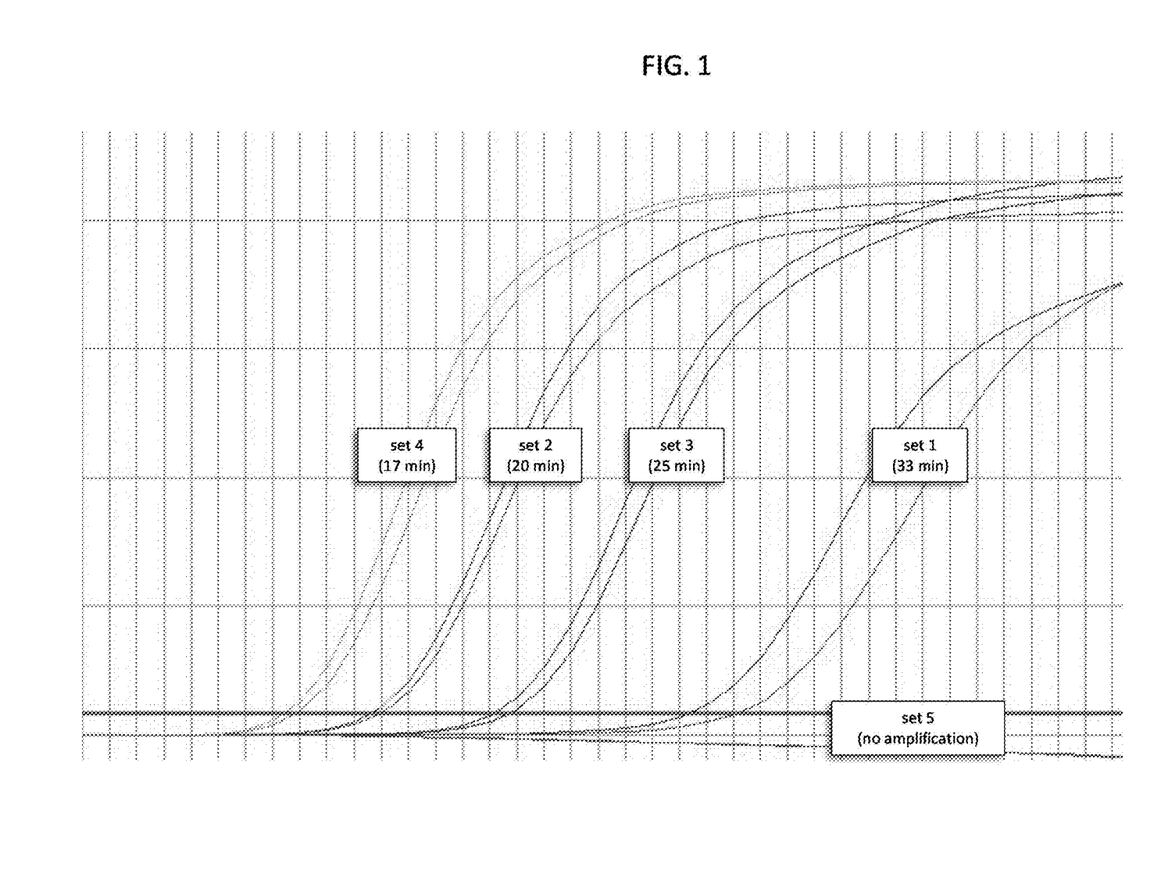
FIG. 1 is a plot showing amplification of *M. pneumoniae* nucleic acids with five candidate sets of LAMP primers. Duplicate samples are shown for each primer set.

One primer set (set 5) resulted in no amplification. The remaining four sets gave varying amplification efficiencies (FIG. 1). Primer sets 2, 3, and 4 were selected for further testing. Set 4 produced amplification in 85/88 no template control (NTC) samples in 60 minutes, and was eliminated from further consideration. Sets 2 and 3 did not give any false positive (0/88) and were screened with potential loop primers using 4:1 $Mg^{2+}:Mn^{2+}$ ratio. A final primer set (Table 2) that included a forward loop primer that decreased amplification time from 27 to 15 minutes was selected.

TABLE 2

| *M. pneumoniae* LAMP primers | | |
|---|---|---|
| Primer | Sequence (5' to 3') | SEQ ID NO: |
| F3 | CCACCTAGTGATTTGGAAGA | 2 |
| B3 | GGACAAAGAAGATTTTCGAAGTT | 3 |

TABLE 2-continued

M. pneumoniae LAMP primers

| Primer | Sequence (5' to 3') | SEQ ID NO: |
|---|---|---|
| FIP | GCTGAACATCAACAAAGAAGGTGCATTGTTGATGAATGTACTACCCA | 4 |
| BIP | ATACCCCACAATTAAGTGGTTGATTCATAGAATATCTGTCCATCTGG | 5 |
| FLP | CTGCACGCATAGTAACAAACTG | 6 |

The LAMP assay protocol reported by Tomita et al. (*Nature Protoc.* 3:877-882, 2008) utilized calcein (25 µM final concentration) and a 16:1 $Mg^{2+}:Mn^{2+}$ ratio (8 mM $MgSO_4$ and 0.5 mM $MnCl_2$). However, in the *M. pneumoniae* LAMP assay, these conditions resulted in high background fluorescence in negative (no template) controls. Two parameters were tested for decreasing the background fluorescence for improved visual readout. Calcein concentrations from 6.25 µM to 25 µM were tested with positive control and NTC samples. Background fluorescence in the NTC samples remained high, even with 6.25 µM calcein (FIG. 2A). The ratio of $Mg^{2+}:Mn^{2+}$ was also tested. Ratios of 8:1 and 4:1 $Mg^{2+}:Mn^{2+}$ with 25 µM calcein reduced background in NTC samples (FIG. 2B). The 4:1 ratio (5.5 mM $MgCl_2$ and 1.375 mM $MnCl_2$) was selected for further experiments.

Example 2

Detection of *M. pneumoniae* by LAMP Assay

This example describes detection of *M. pneumoniae* in clinical samples using a LAMP assay.

Figure 3A:
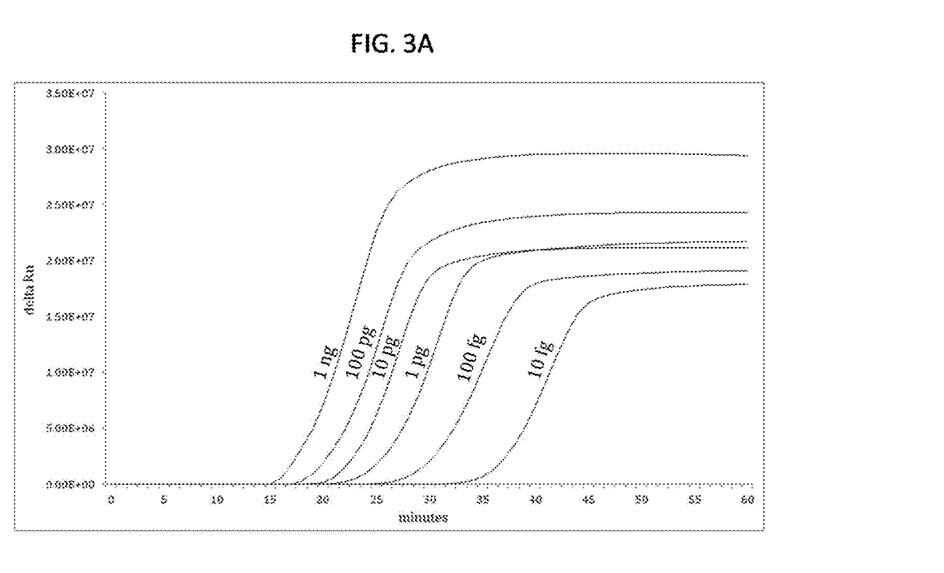
FIG. 3A is a graph showing amplification of serial dilutions of *M. pneumoniae* DNA.
Figure 3B:
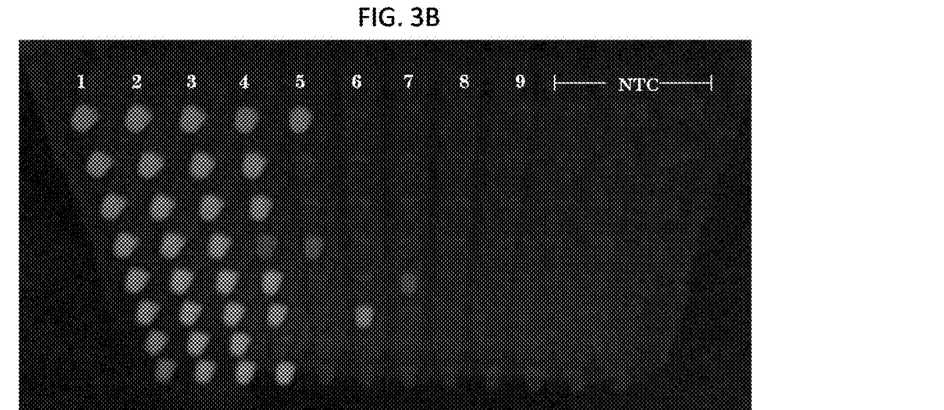
FIG. 3B is a digital image showing the visual readout of amplification with serial dilutions of *M. pneumoniae* DNA in a 96 well plate. Column 1, 10 ng; column 2, 1 ng; column 3, 100 pg; column 4, 10 pg; column 5, 1 pg; column 6, 100 fg; column 7, 10 fg; column 8, 1 fg; column 9, 100 ag; NTC, no template control.
Figure 4:
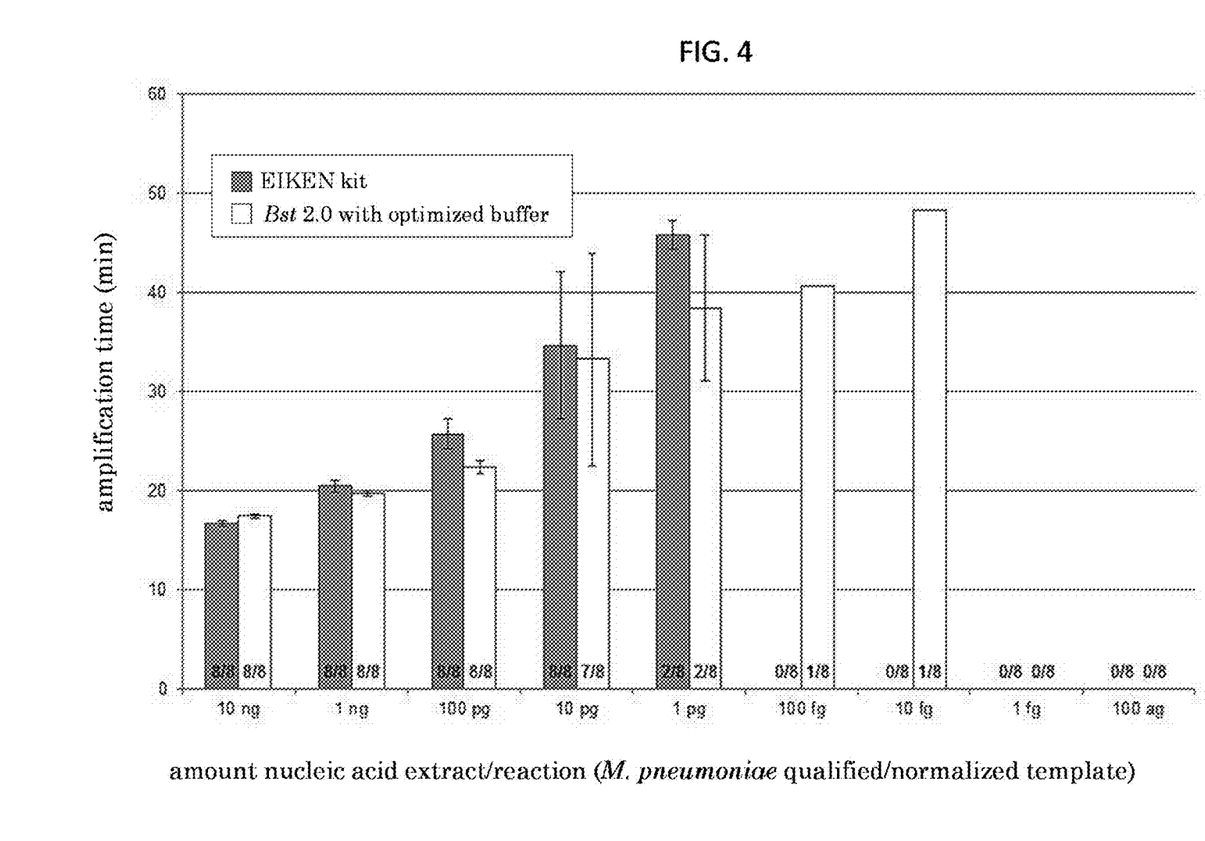
FIG. 4 is a graph of the data presented in FIG. 3B, showing amplification time for serial dilutions of *M. pneumoniae* in a LAMP assay using reagents from LoopAmp kit (Eiken Chemical Corp.) or optimized reaction buffer with Bst 2.0 polymerase.

The LAMP assay primers and conditions were as described in Example 1. In some experiments, specimens and extracts were also tested with a validated real-time PCR (qPCR) assay as described in Winchell et al. (*J. Clin. Microbiol.* 46:3116-3118, 2008). The sensitivity of the assay was tested using serial dilutions of *M. pneumoniae* M129 DNA. The analytical sensitivity of the assay was 10 fg (FIGS. 3A and 3B). The optimized reaction mix performed similarly to the LoopAmp reaction mix (Eiken); however, the optimized reaction mix produced amplification in 1/8 reactions with 100 fg or 10 fg of extracted nucleic acid, while the LoopAmp mix did not produce any amplification product at these DNA concentrations (FIG. 4).

Figure 5:
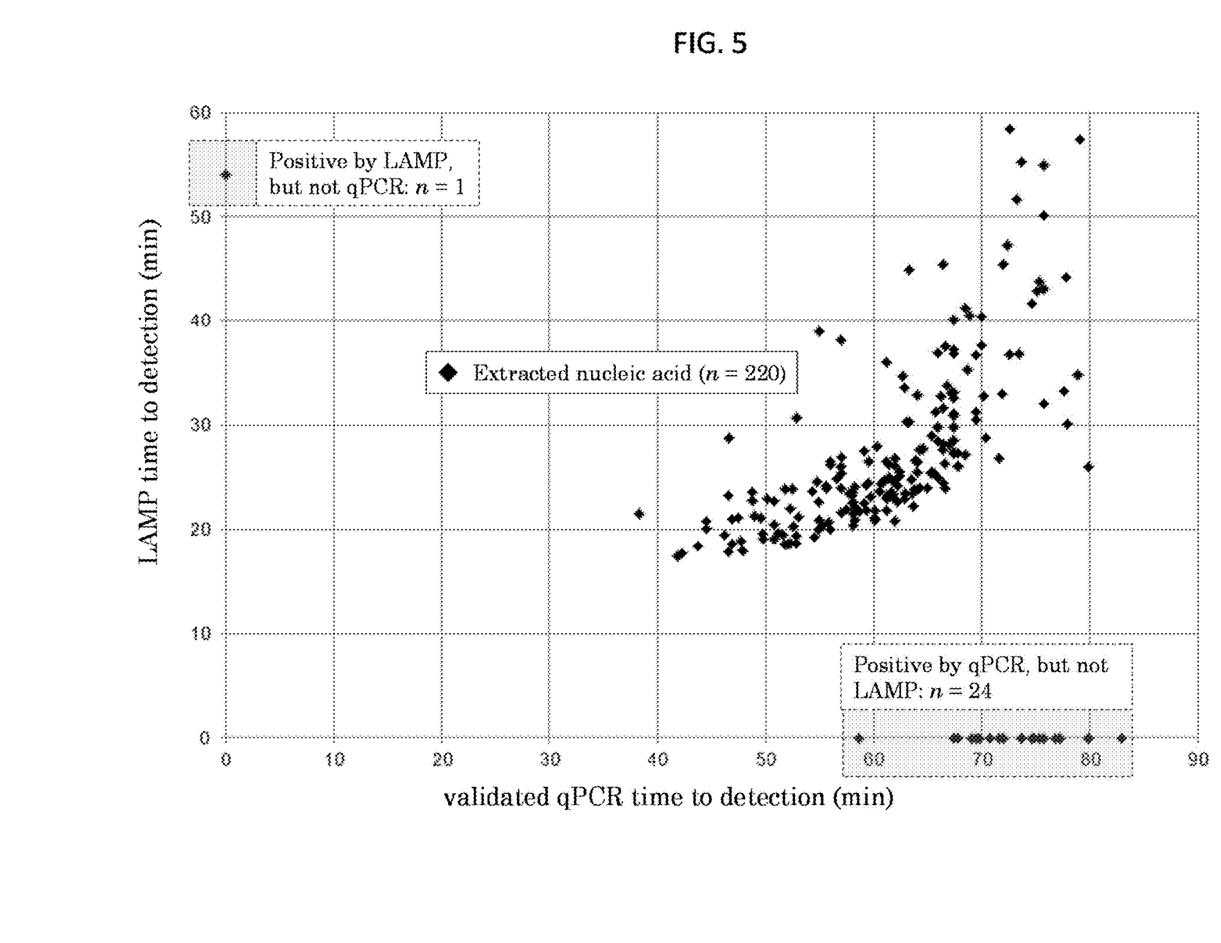
FIG. 5 is a graph showing time to detection with the CARDS toxin LAMP assay (y-axis) or real-time PCR assay (qPCR, x-axis) using extracted nucleic acid samples.

Time to detection was assessed for both the *M. pneumoniae* LAMP assay and qPCR assay on extracted nucleic acids from a set of 220 samples. The LAMP assay detected the *M. pneumoniae* nucleic acids sooner than the qPCR assay (FIG. 5). The LAMP assay was 88% as sensitive as the qPCR assay when tested on extracts derived from clinical specimens (Table 3). However, 24/26 (92%) of the *M. pneumoniae* positives that were negative with the LAMP assay had a qPCR Ct>30. If the qPCR Ct was <30, there was a 99% correlation for LAMP and qPCR.

TABLE 3

Sensitivity of LAMP compared to qPCR

| qPCR positive | 219 | LAMP positive | 193 (88.1%) |
| | | LAMP negative | 26 (11.8%) |
| qPCR negative | 26 | LAMP positive | 1 (3.8%) |
| | | LAMP negative | 25 (96.1%) |

A smaller cohort of *M pneumoniae*-positive specimens determined by qPCR (using extracted nucleic acid samples) were tested with LAMP, by addition of 5 µl of unextracted specimen in universal transport media (UTM) to the reaction (Table 4). Independent experiments indicated that the diluent used impacts detection time. LAMP detection of *M. pneumoniae* stock resuspended in UTM was about 5 minutes later than for the same stock resuspended in TE buffer or water.

TABLE 4

Direct testing of primary specimens with LAMP

| | Nucleic acid positive (qPCR) | Specimen positive (LAMP) |
|---|---|---|
| BAL | 6 | 4 |
| NP/OP | 16 | 8 |
| Nasal wash | 37 | 10 |

BAL, bronchoalveolar lavage;
NP/OP, nasopharyngeal/oropharyngeal swab

Example 3

Detection of *M. pneumoniae* Nucleic Acids Using LAMP

This example describes particular methods useful for detecting *M. pneumoniae* nucleic acid in a sample using an LAMP assay. However, one skilled in the art will appreciate that methods that deviate from these specific methods can also be used to successfully detect *M. pneumoniae* nucleic acids in a sample.

Clinical samples are obtained from a subject (such as a subject suspected of having a *M. pneumoniae* infection), such as a BAL, NP/OP swab, or nasal wash sample. Typically, the sample is used directly or with minimal processing (for example, dilution and/or vortexing in water or buffer, and optionally chemical or heat disruption). However, DNA can be extracted from the sample using routine methods (for example using a commercial kit) if desired.

LAMP is performed in a reaction including a reaction mix (e.g., buffers, $MgCl_2$, $MnCl_2$, dNTPs, calcein, and DNA polymerase), sample (5-10 µl of unextracted sample or 1-10 µl of nucleic acid extracted from the sample), and primers. The primers are included in the reaction as follows: F3 (SEQ ID NO: 2) and B3 (SEQ ID NO: 3) at 0.2 µM, FIP (SEQ ID NO: 4) and BIP (SEQ ID NO: 5) at 1.6 µM, and Loop F (SEQ ID NO: 6) at 0.8 µM. The assay is incubated at about 60-65° C. (for example, about 62-63° C.) for about 1 hour and the reaction is terminated by incubation at 80° C. for about 2 minutes. Samples are examined visually under an ultraviolet lamp or fluorescence is detected using an instrument such as a real-time PCR platform (e.g., ABI 7500 platform) or basic fluorimeter. Positive samples are those with observable fluorescence greater than that in a reagent only (no sample) control tube or other negative control.

In some examples, a subject from whom a positive sample is obtained is administered one or more therapeutic agents for treatment of *M. pneumoniae* infection, such as one or more antibiotics (for example, one or more macrolide, tetracycline, or fluoroquinolone antibiotics).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A kit comprising a set of loop-mediated isothermal amplification (LAMP) primers specific for a *Mycoplasma pneumoniae* nucleic acid, comprising primers consisting of:

CCACCTAGTGATTTGGAAGA; (SEQ ID NO: 2)

GGACAAAGAAGATTTTCGAAGTT; (SEQ ID NO: 3)

GCTGAACATCAACAAAGAAGGTGCATTGTTGATGAATGTACTACCCA; (SEQ ID NO: 4) and

ATACCCCACAATTAAGTGGTTGATTCATAGAATATCTGTCCATCTGG. (SEQ ID NO: 5)

2. The kit of claim 1, further comprising a forward loop primer consisting of the nucleic acid sequence CTGCACGCATAGTAACAAACTG (SEQ ID NO: 6).

3. The kit of claim 1, further comprising a fluorescent indicator dye.

4. The kit of claim 3, wherein the fluorescent indicator dye comprises calcein.

5. The kit of claim 1, further comprising a buffer comprising a ratio of 4:1 $Mg^{2+}$ to $Mn^{2+}$.

6. The kit of claim 5, wherein the buffer comprises 20 mM Tris (pH 8.8), 10 mM KCl, 5.5 mM $MgSO_4$, 10 mM $(NH_4)_2SO_4$, 0.1% TWEEN-20, 0.8 M betaine, and 1.375 mM $MnCl_2$.

7. A method of detecting presence of *Mycoplasma pneumoniae* in a sample, comprising:

contacting the sample with the set of loop-mediated isothermal amplification (LAMP) primers of the kit of claim 1 under conditions sufficient for amplification of the *M. pneumoniae* nucleic acid; and detecting the *M. pneumoniae* amplification product, thereby detecting presence of *M. pneumoniae* in the sample.

8. The method of claim 7, wherein the set of LAMP primers further comprises a forward loop primer consisting of the nucleic acid sequence CTGCACGCATAG-TAACAAACTG (SEQ ID NO: 6).

9. The method of claim 7, wherein detecting the *M. pneumoniae* amplification product comprises determining turbidity, color, or fluorescence of the sample.

10. The method of claim 7, further comprising contacting the sample with a fluorescent indicator dye.

11. The method of claim 10, wherein the fluorescent indicator dye comprises calcein or hydroxynaphthol blue.

12. The method of claim 11, further comprising contacting the sample with the LAMP primers in a buffer comprising a ratio of 4:1 $Mg^{2+}$ to $Mn^{2+}$.

\* \* \* \* \*